US012042389B2

(12) United States Patent
Brandewie et al.

(10) Patent No.: US 12,042,389 B2
(45) Date of Patent: Jul. 23, 2024

(54) APPARATUS AND METHOD FOR INSTALLING AN ACETABULAR LINER ON AN ACETABULAR CUP

(71) Applicant: DePuy Ireland Unlimited Company, Ringaskiddy (IE)

(72) Inventors: Alena M. Brandewie, Warsaw, IN (US); Ryan C. Keefer, Warsaw, IN (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 399 days.

(21) Appl. No.: 17/246,106

(22) Filed: Apr. 30, 2021

(65) Prior Publication Data
US 2022/0346960 A1     Nov. 3, 2022

(51) Int. Cl.
*A61F 2/34*     (2006.01)
*A61F 2/46*     (2006.01)
*A61F 2/30*     (2006.01)

(52) U.S. Cl.
CPC .............. *A61F 2/34* (2013.01); *A61F 2/4609* (2013.01); *A61F 2002/30428* (2013.01); *A61F 2002/3429* (2013.01)

(58) Field of Classification Search
CPC ....................... A61F 2/34; A61F 2/4609; A61F 2002/30428; A61F 2002/3429; A61F 2002/3401; A61F 2002/3403; A61F 2002/4629
See application file for complete search history.

(56) References Cited

U.S. PATENT DOCUMENTS

| 3,829,904 A | 8/1974 | Ling et al. |
| 3,863,273 A | 2/1975 | Averill |
| 4,714,477 A | 12/1987 | Fichera et al. |
| 5,133,763 A | 7/1992 | Mullers |
| 5,156,626 A | 10/1992 | Broderick et al. |

(Continued)

FOREIGN PATENT DOCUMENTS

| GB | 2152385 A | 8/1985 |
| WO | 9522944 A1 | 8/1995 |

OTHER PUBLICATIONS

PCT International Search Report for International Application No. PCT/EP2022/061517, Aug. 16, 2022, 5 pages.

*Primary Examiner* — Brian A Dukert
*Assistant Examiner* — Melissa A Hoban
(74) *Attorney, Agent, or Firm* — Barnes & Thornburg LLP

(57) ABSTRACT

An acetabular prosthesis assembly includes an acetabular shell component and an acetabular bearing component. The shell component includes a concave inner wall having a tapered surface with multiple anti-rotation slots defined therein. The bearing component includes a convex outer wall as well as an annular flange and multiple anti-rotation keys extending radially outward from the outer wall. When the anti-rotation keys are positioned in rotational alignment with the anti-rotation slots, the flange of the bearing component is positioned in contact with the tapered surface of the shell component. When the anti-rotation keys are positioned out of rotational alignment with the anti-rotation slots, the flange is spaced apart from the tapered surface. Methods for assembling and using the acetabular prosthesis assembly are also disclosed.

17 Claims, 14 Drawing Sheets

(56) References Cited

U.S. PATENT DOCUMENTS

| | | | |
|---|---|---|---|
| 5,282,864 A * | 2/1994 | Noiles | A61F 2/30721 623/23.43 |
| 5,425,779 A | 6/1995 | Schlosser et al. | |
| 5,458,649 A | 10/1995 | Spotorno et al. | |
| 5,549,691 A | 8/1996 | Harwin | |
| 5,879,401 A | 3/1999 | Besemer et al. | |
| 6,488,713 B1 | 12/2002 | Hershberger | |
| 7,153,328 B2 | 12/2006 | Kim | |
| 7,192,449 B1 | 3/2007 | McQueen et al. | |
| 7,402,177 B2 | 7/2008 | Jones et al. | |
| 7,819,925 B2 | 10/2010 | King et al. | |
| 7,833,452 B2 | 11/2010 | Muratoglu et al. | |
| 8,123,815 B2 * | 2/2012 | Meridew | A61F 2/34 623/22.29 |
| 8,177,851 B2 | 5/2012 | Drescher | |
| 8,293,811 B2 | 10/2012 | Muratoglu et al. | |
| 8,308,810 B2 * | 11/2012 | Meridew | A61F 2/34 623/22.19 |
| 8,461,225 B2 | 6/2013 | Muratoglu et al. | |
| 8,679,187 B2 | 3/2014 | Allen et al. | |
| 8,771,367 B2 | 7/2014 | Armacost et al. | |
| 8,801,798 B1 | 8/2014 | Smith | |
| 8,840,676 B2 | 9/2014 | Belew et al. | |
| 8,858,645 B2 | 10/2014 | Grostefon et al. | |
| 8,888,859 B2 | 11/2014 | Muratoglu et al. | |
| 9,168,683 B2 | 10/2015 | Muratoglu et al. | |
| 10,307,255 B1 | 6/2019 | Hutton et al. | |
| 10,383,745 B2 * | 8/2019 | Allen | A61F 2/30767 |
| 11,413,152 B2 * | 8/2022 | Albert | A61F 2/4609 |
| 2001/0037156 A1 | 11/2001 | Burstein et al. | |
| 2003/0105529 A1 | 6/2003 | Snyder et al. | |
| 2003/0144742 A1 | 7/2003 | King et al. | |
| 2004/0117029 A1 | 6/2004 | Lewis et al. | |
| 2004/0199257 A1 | 10/2004 | Dooney | |
| 2005/0146070 A1 | 7/2005 | Muratoglu et al. | |
| 2007/0106392 A1 | 5/2007 | Servidio et al. | |
| 2007/0118227 A1 | 5/2007 | King et al. | |
| 2007/0203583 A1 | 8/2007 | Slone | |
| 2007/0250175 A1 | 10/2007 | Meridew et al. | |
| 2008/0215142 A1 | 9/2008 | Muratoglu et al. | |
| 2010/0082101 A1 | 4/2010 | Muratoglu et al. | |
| 2010/0131073 A1 | 5/2010 | Meridew et al. | |
| 2012/0089235 A1 | 4/2012 | Conway et al. | |
| 2012/0185059 A1 | 7/2012 | Vankoski et al. | |
| 2012/0319332 A1 | 12/2012 | Mcminn | |
| 2013/0245775 A1 | 3/2013 | Metcalfe | |
| 2013/0325139 A1 | 12/2013 | Steiner et al. | |
| 2017/0086980 A1 | 3/2017 | Suckow | |
| 2020/0205987 A1 | 7/2020 | Brandewie et al. | |

* cited by examiner

APPARATUS AND METHOD FOR INSTALLING AN ACETABULAR LINER ON AN ACETABULAR CUP

TECHNICAL FIELD

The present disclosure relates generally to orthopaedic surgical implants and, more particularly, to modular orthopaedic surgical implant systems.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A typical prosthetic hip joint includes an acetabular prosthetic component and a femoral head prosthetic component. An acetabular prosthetic component generally includes an outer shell or cup configured to engage the acetabulum of the patient and an inner bearing or liner coupled to the shell and configured to engage the femoral head. The femoral head prosthetic component and inner bearing of the acetabular component form a ball and socket joint that approximates the natural hip joint.

SUMMARY

According to one aspect, an acetabular prosthesis assembly includes an acetabular shell component configured to be implanted in a surgically-prepared acetabulum of a patient and a polymeric acetabular bearing component configured to be received by the acetabular shell component. The acetabular shell component includes an annular rim and a concave inner wall extending medially from the annular rim, the concave inner wall having a tapered surface with a plurality of anti-rotation slots defined therein. The acetabular bearing component includes an annular rim, a convex outer wall extending medially from the annular rim to an apex, an annular flange extending radially outward from the outer wall, and a plurality of anti-rotation keys extending radially outward from the outer wall. When the plurality of anti-rotation keys are positioned in rotational alignment with the plurality of anti-rotation slots, the flange of the acetabular bearing component is positioned in contact with the tapered surface of the acetabular shell component. When the plurality of anti-rotation keys are positioned out of rotational alignment with the plurality of anti-rotation slots, the flange of the acetabular bearing component is spaced apart from the tapered surface of the acetabular shell component.

In an embodiment, when the plurality of anti-rotation keys are positioned out of rotational alignment with the plurality of anti-rotation slots, a medial surface of each of the plurality of anti-rotation keys is positioned in contact with the annular rim of the acetabular shell component. In an embodiment, when the plurality of anti-rotation keys are positioned in rotational alignment with the plurality of anti-rotation slots, the medial surface of each of the plurality of anti-rotation keys is positioned within a corresponding anti-rotation slot of the plurality of anti-rotation slots. In an embodiment, when the plurality of anti-rotation keys are positioned in rotational alignment with the plurality of anti-rotation slots, the medial surface of each of the plurality of anti-rotation keys is positioned medially by a predetermined distance from the annular rim of the acetabular shell component. In an embodiment, the predetermined distance is 0.5 millimeters.

In an embodiment, the plurality of anti-rotation keys are spaced evenly around the annular rim of the acetabular bearing component.

In an embodiment, when the plurality of anti-rotation keys are positioned in rotational alignment with the plurality of anti-rotation slots and the acetabular bearing component is fully installed in the acetabular shell component, each of the plurality of anti-rotation keys is positioned within a corresponding anti-rotation slot of the plurality of anti-rotation slots. In an embodiment, when the plurality of anti-rotation keys are positioned in rotational alignment with the plurality of anti-rotation slots and the acetabular bearing component is fully installed in the acetabular shell component, the flange is received in an annular groove defined in the concave inner wall of the acetabular shell component.

In an embodiment, the outer wall of the acetabular bearing component includes a tapered surface extending medially from the annular rim. In an embodiment, each of the plurality of anti-rotation keys comprises an outer wall that blends into the tapered surface. In an embodiment, the plurality of anti-rotation keys extend radially outward from the tapered surface. In an embodiment, the outer wall of the acetabular bearing component includes a curved relief surface positioned between the tapered surface and the flange, wherein the curved relief surface extends radially inward from the tapered surface and the flange.

In an embodiment, the tapered surface of the acetabular shell component defines a taper angle, and the flange of the acetabular bearing component comprises a flange surface that defines a flange angle. The flange angle is greater than or equal to the taper angle. In an embodiment, the taper angle is 10° and the flange angle is between 10-14°. In an embodiment, the flange angle is 12°.

According to another aspect, a method for installing an acetabular prosthesis includes implanting an acetabular shell component into a surgically-prepared acetabulum of a patient, wherein the acetabular shell component comprises an annular rim and a concave inner wall extending medially from the annular rim, the concave inner wall having a tapered surface with a plurality of anti-rotation slots defined therein; moving an acetabular bearing component into contact with the implanted acetabular shell component in response to implanting the acetabular shell component, wherein the acetabular bearing component comprises (i) an annular rim, (ii) a convex outer wall extending medially from the annular rim to an apex, (iii) an annular flange extending radially outward from the outer wall, and (iv) a plurality of anti-rotation keys extending radially outward from the outer wall; and rotating the acetabular bearing component relative to the implanted acetabular shell component from a first position in which the plurality of anti-rotation keys are positioned out of rotational alignment with the plurality of anti-rotation slots to a second position in which the plurality of anti-rotation keys are positioned in rotational alignment with the plurality of anti-rotation slots, wherein when in the first position the flange of the acetabular bearing component is spaced apart from the tapered surface of the acetabular shell component, and when in the second position the flange of the acetabular bearing component is positioned in contact with the tapered surface of the acetabular shell component.

In an embodiment, the method further includes impacting the acetabular bearing component into the implanted acetabular shell component once the acetabular bearing component is in the second position.

In an embodiment, impacting the acetabular bearing component includes deforming the flange of the acetabular bearing component. In an embodiment, the method further includes receiving the flange of the acetabular bearing component in an annular groove defined in the concave inner wall of the acetabular shell component. In an embodiment, receiving the flange in the annular groove includes elastomerically relaxing the flange to its original shape. In an embodiment, the receiving the flange in the annular groove comprises engaging a tapered surface of the acetabular bearing component with the tapered surface of the acetabular shell component.

BRIEF DESCRIPTION OF THE DRAWINGS

The detailed description particularly refers to the following figures, in which.

DETAILED DESCRIPTION OF THE DRAWINGS

Figure 1:
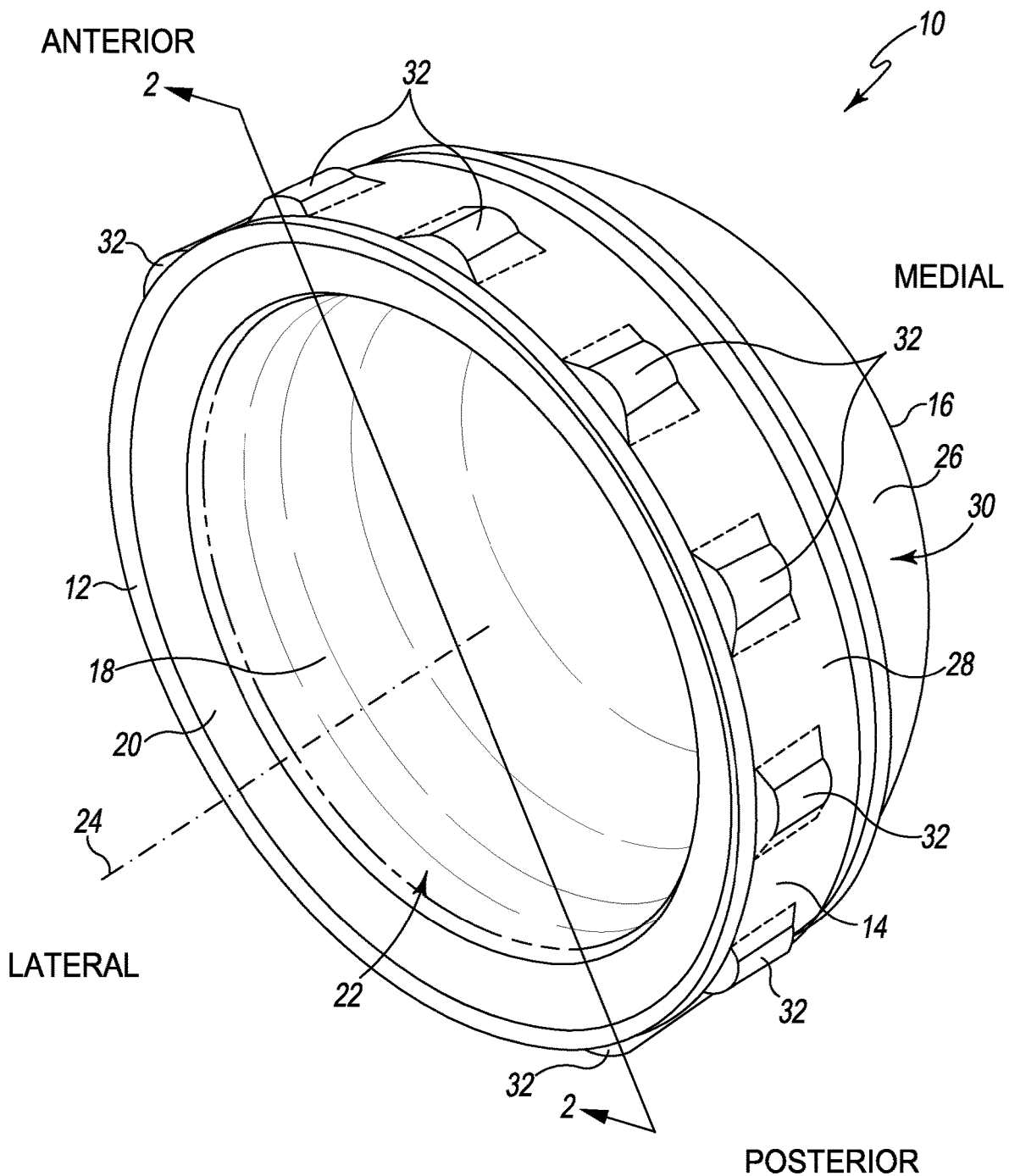
FIG. 1 is a perspective view of an acetabular bearing component of an acetabular prosthetic implant.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 2:
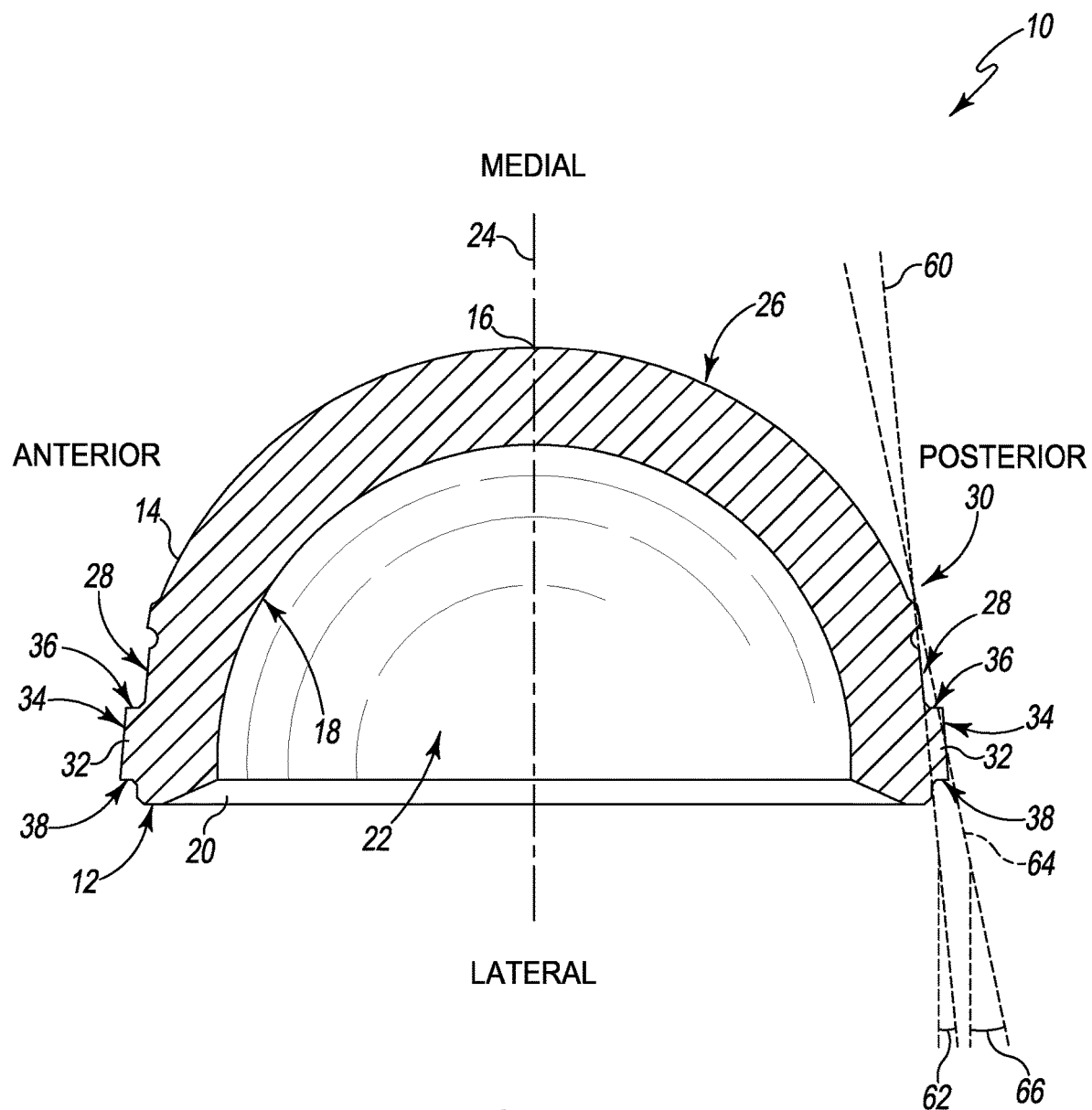
FIG. 2 is a cross-sectional view taken in the anterior-posterior direction along the line 2-2 of FIG. 1, as viewed in the direction of the arrows.
Figure 3:
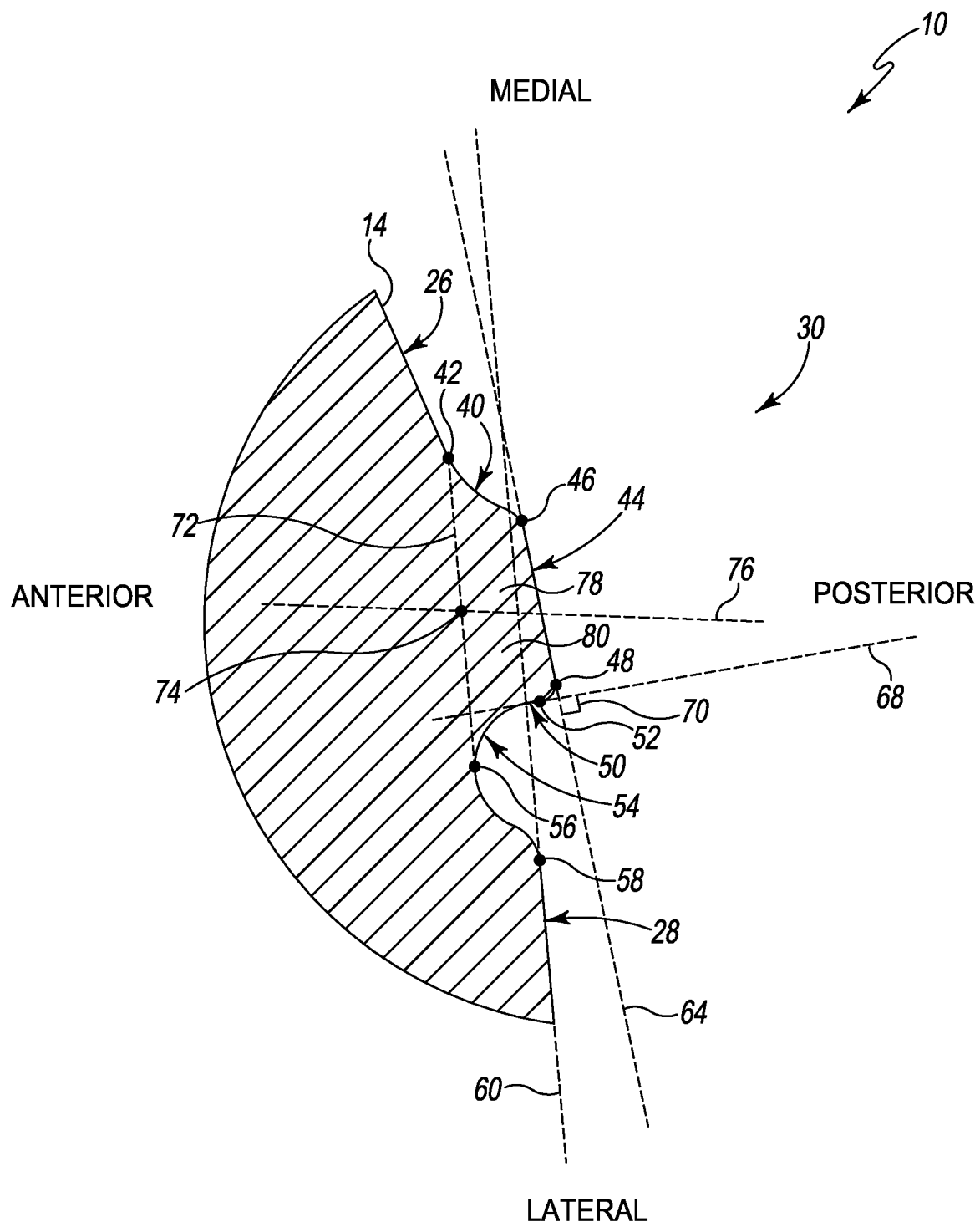
FIG. 3 is a detail view of the cross-sectional view of FIG. 2.

Referring now to FIGS. 1-3, an illustrative acetabular prosthesis includes an acetabular bearing 10. The bearing 10 is formed from a polymeric material such as ultra-high-molecular-weight (UHMW) polyethylene (PE), highly crosslinked PE, antioxidant filled PE, or other polymers such as polyether ether ketone (PEEK). The bearing 10 has an annular rim 12 and a convex outer surface 14 that extends medially from the annular rim 12 to an apex 16. A concave inner surface 18 extends inward from the annular rim 12. In some embodiments, an angled chamfer 20 may separate the annular rim 12 and the concave inner surface 18. The inner surface 18 defines a cavity 22, which is sized to receive a prosthetic component such as a femoral head component (not shown), which may be formed from a metallic material, a ceramic material, or other material. In other embodiments, the cavity 22 may be sized to receive a mobile bearing, a captive femoral head, or other prosthetic component. The cavity 22 further defines a polar axis 24. The polar axis 24 may be an axis of rotation; that is, the acetabular bearing 10 may be rotationally symmetrical about the axis 24.

The outer surface 14 of the bearing 10 includes a hemispherical surface 26 extending laterally from the apex 16 and a tapered surface 28 extending medially from the annular rim 12. An annular flange 30 is positioned between the hemispherical surface 26 and the tapered surface 28 and extends radially outward from the outer surface 14. As described further below, in use the tapered surface 28 allows for a friction lock between the acetabular bearing 10 and an acetabular shell component, and the flange 30 provides mechanical pull-out and spin-out resistance for the acetabular bearing 10.

The acetabular bearing 10 further includes multiple anti-rotation keys 32 that each extend radially outward from the tapered surface 28. The anti-rotation keys 32 are evenly distributed around the circumference of the tapered surface 28. As best shown in FIG. 2, each anti-rotation key 32 includes an outer surface 34, a medial surface 36, and a lateral surface 38. The outer surface 34 of each anti-rotation key 32 blends smoothly into the tapered surface 28, and the medial surface 36 of each anti-rotation key 32 forms a ledge projecting outward from the tapered surface 28. As described further below, the anti-rotation keys 32 cooperate with corresponding anti-rotation slots of the acetabular shell component to rotationally align the acetabular bearing 10 and the acetabular shell component. Additionally, although illustrated as including 12 anti-rotation keys 32, it should be understood that in other embodiments the acetabular bearing 10 may include a different number of anti-rotation keys 32.

As shown in FIG. 3, the outer surface 14 of the acetabular bearing 10 further includes a curved lead-in surface 40 that extends laterally from the hemispherical surface 26. A tangent point 42 is positioned at the transition between the hemispherical surface 26 and the curved lead-in surface 40. The tangent point 42 is a point of tangency in a geometrical sense. That is, for the curve defined by the outer surface 14 at the transition between the hemispherical surface 26 and the curved lead-in surface 40, a single tangent line exists that passes through the tangent point 42. Thus, the transition between the hemispherical surface 26 and the curved lead-in surface 40 is smooth, without discontinuities.

A flat flange surface 44 extends laterally from the curved lead-in surface 40. A tangent point 46 is positioned at the transition between the curved lead-in surface 40 and the flat flange surface 44. Again, this means that the transition between the surfaces 40, 44 is smooth, without discontinuities. A back edge surface 50 extends laterally from the flat flange surface 44. Similarly, a pair of tangent points 48, 52 are positioned between the flange surface 44 and the back edge surface 50. As shown, the tangent point 48 is positioned between the flange surface 44 and a curved corner of the back edge surface 50, and the tangent point 52 is positioned between the curved corner and a flat portion of the back edge surface 50.

A curved relief surface 54 extends laterally from the back edge surface 50. Illustratively, the relief surface 54 curves inward from the outer surface to an inner-most point 56 and then curves outward to the tapered surface 28. The tapered surface 28 extends laterally from the curved relief surface 56 to the annular rim 12, shown in FIGS. 1-2. A tangent point 58 is positioned at the transition between the relief surface 54 and the tapered surface 28.

As shown in FIGS. 2-3, an imaginary line 60 extends along the tapered surface 28. The imaginary line 60 and the polar axis 24 define an angle 62, which is illustratively 5.1°. Thus, because the acetabular bearing 10 is rotationally symmetrical about the polar axis 24, in the illustrative embodiment the opposing tapered surfaces 28 on either side of the acetabular bearing 10 (e.g., on each of the anterior side and the posterior side, each of the superior side and the inferior side, or any other pair of opposing side) define a taper angle of 10.2° (i.e., twice the angle 62). As described further below, this taper angle is slightly larger than the corresponding taper angle of the acetabular shell component, which is 10° in the illustrative embodiment. Of course, in other embodiments a different angle 62 (and thus a different taper angle) may be used.

As shown in FIG. 3, the flange surface 44 extends outward past the imaginary line 60. That is, the imaginary line 60 is positioned between the flange surface 44 and the inner surface 18. In contrast, the relief surface 54 extends inward relative to the imaginary line 60. In other words, the relief surface 54 is positioned between the imaginary line 60 and the inner surface 18. As described further below, in use the flange surface 44, extending radially outward further than the tapered surface 28, contacts a corresponding tapered surface of the acetabular shell component. As the acetabular bearing 10 is inserted, the flange 30 deforms. The relief surface 54 provides stress relief for the flange 30 such that, when fully inserted, the flange 30 may return to its original shape without plastic deformation.

As further shown in FIGS. 2-3, another imaginary line 64 extends along the flange surface 44. The imaginary line 64 and the polar axis 24 define an angle 66, which is illustratively 12°. The angle 66 defined by the imaginary line 64 and the polar axis 24 is greater than the angle 62 defined by the imaginary line 60 and the polar axis 24. Additionally, although illustrated as 12°, it should be understood that in other embodiments, the angle 66 may have a different value. For example, in some embodiments, the angle 66 may be within the range of 10°-14°. As another example, the angle 66 may be about two degrees larger than the taper angle of the acetabular bearing 10.

Another imaginary line 68 extends along the back edge surface 50 and intersects with the imaginary line 64. The imaginary lines 64, 68 define an angle 70, which is illustratively 90°. As described further below, the back edge surface 50 may provide increased pull-out resistance for the acetabular bearing 10.

As shown in FIG. 3, an imaginary line segment 72 extends from the tangency point 42, at the transition between the hemispherical surface 26 and the curved lead-in surface 40, to the inner-most point 56 of the relief surface 54. The line segment 72 represents a boundary of the flange 30, and thus the flange 30 includes material positioned between the line segment 72 and the outer surface 14. The line segment 72 includes a midpoint 74, and an imaginary dividing line 76 intersecting the midpoint 74 extends parallel to the annular rim 12 in the anterior-posterior direction. The dividing line 76 separates the cross-sectional area bounded by the line segment 72 and the outer wall 14 into a medial area 78 and a lateral area 80. The medial area 78 is bounded by the line segment 72, the dividing line 76, and the outer wall 14, and is positioned on the medial side of the dividing line 76 (i.e., toward the apex 16). Similarly, the lateral area 80 is bounded by the line segment 72, the dividing line 76, and the outer wall 14, but is positioned on the lateral side of the dividing line 76 (i.e., toward the annular rim 12). The lateral area 80 is larger than the medial area 78. For example, in some embodiments, the lateral area 80 may represent about 51% of the cross-sectional area bounded by the line segment 72 and the outer wall 14. Because the lateral area 80 is larger than the medial area 78, this means that a majority of the material of the flange 30 is positioned laterally of the dividing line 76.

Referring now to FIGS. 4-7, the illustrative acetabular prosthesis further includes an acetabular shell component 100. The acetabular prosthetic shell component 100 is shaped to be implanted in a surgically-prepared acetabulum of a patient's pelvis and, as described further below, the shell component 100 is configured to receive the acetabular bearing 10. The shell component 100 is formed from an implant-grade metallic material such as cobalt chromium or titanium. The shell component 100 has an annular rim 102 and an outer wall 104 that extends medially from the annular rim 102. The outer wall 104 includes an annular outer surface 106 that extends from the annular rim 102 to a convex curved outer surface 108. In the illustrative embodiment, the convex curved outer surface 108 is semi-spherical and shaped to match the shape of a patient's surgical prepared acetabulum. The shell component 100 also includes a Porocoat® outer coating 110 that permits bone to affix biologically to the shell component 100 after implantation. The Porocoat® outer coating 110 covers the outer surface 108 and follows its geometric shape. It should be appreciated that in other embodiments the Porocoat® outer coating 110 may be omitted.

The shell component 100 further includes an inner wall 112 that extends inwardly from the annular rim 102 to define a cavity 114 in the shell component 100. The illustrative cavity 114 is sized to receive the acetabular bearing 10 described above. The concave inner wall 112 further defines a polar axis 116 extending through the cavity 114. Similar to the polar axis 24 of the acetabular bearing 10, the polar axis 116 may be an axis of rotation; that is, the acetabular shell component 100 may be rotationally symmetrical about the axis 116.

Figure 5:
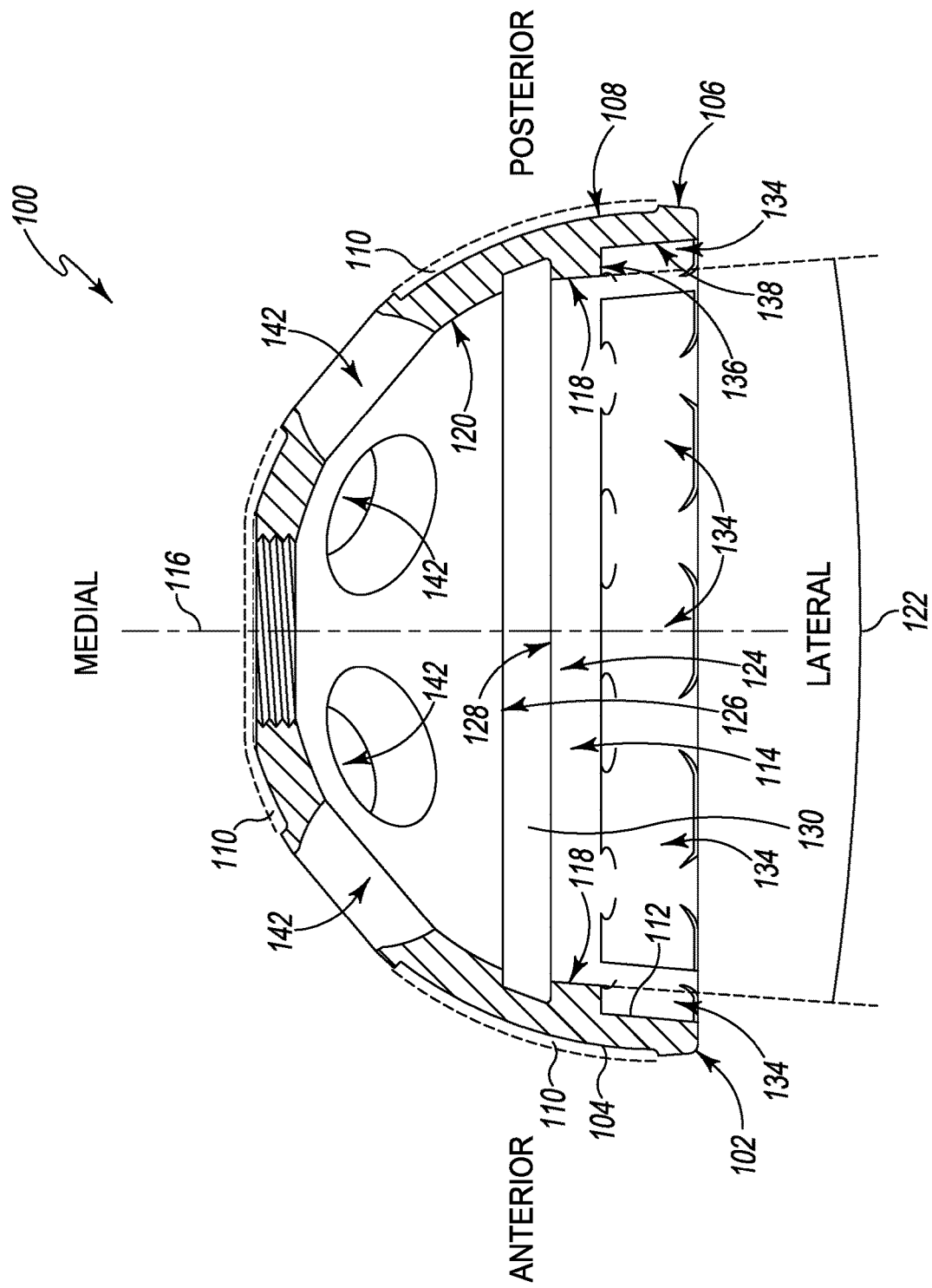
FIG. 5 is a cross-sectional view taken in the anterior-posterior direction along the line 5-5 of FIG. 4, as viewed in the direction of the arrows.

The inner wall 112 of the shell component 100 further includes an annular, tapered surface 118 that extends inwardly from the annular rim 102, and a hemispherical surface 120 that extends further inwardly from the tapered surface 118. As shown in FIG. 5, the opposing tapered surfaces 118 on either side of the shell component 100 (e.g., on each of the anterior side and the posterior side, each of the superior side and the inferior side, or any other pair of opposing sides) define a taper angle 122. Illustratively, the taper angle 122 for the shell component 100 is 10°, although in other embodiments the taper angle 122 may have a different amount.

Figure 6:
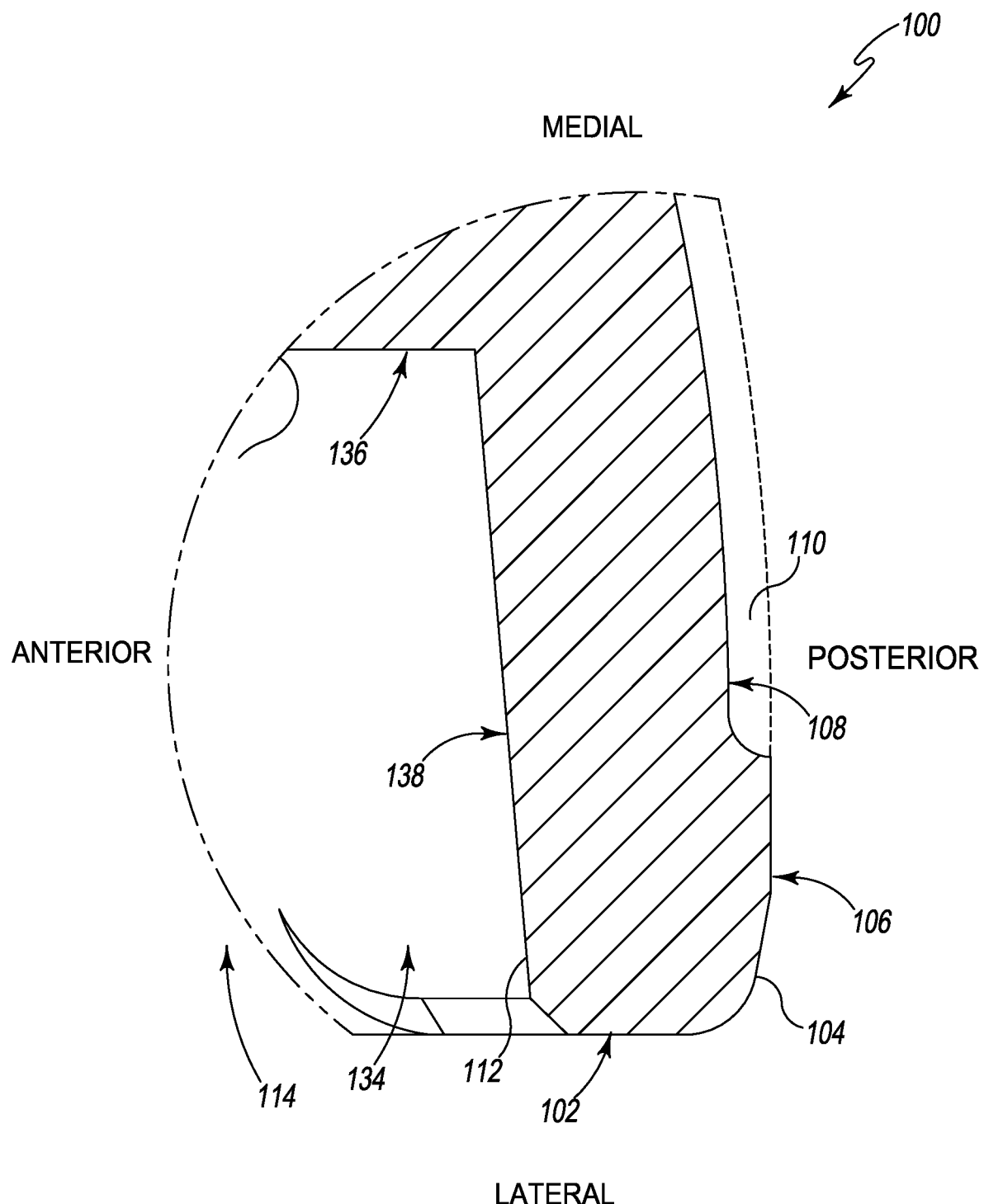
FIG. 6 is a detail view of the cross-sectional view of FIG. 5.
Figure 7:
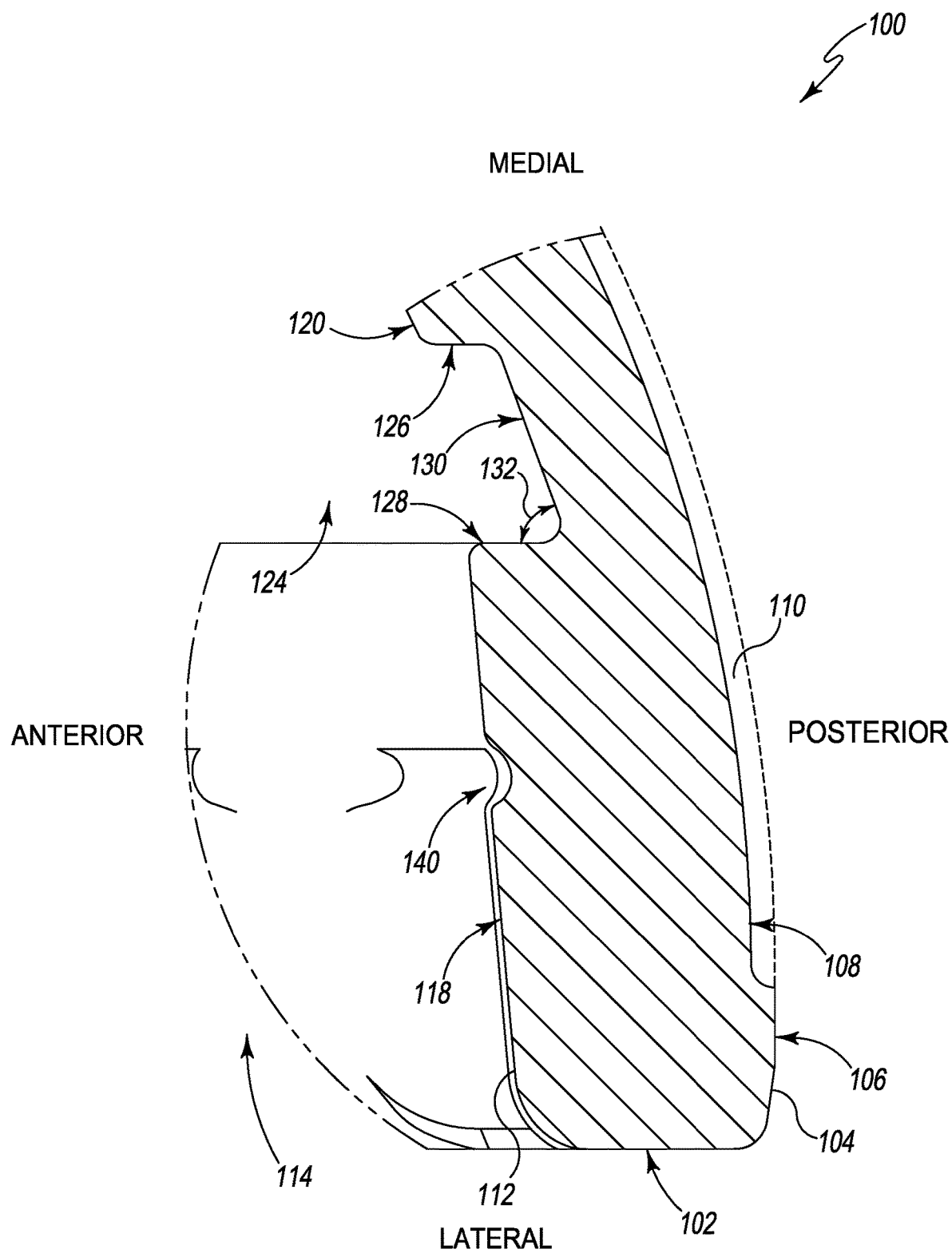
FIG. 7 is a detail cross-sectional view taken in the anterior-posterior direction along the line 7-7 of FIG. 4, as viewed in the direction of the arrows.

An annular groove 124 is defined in the inner wall 112 between the tapered surface 118 and the hemispherical surface 120. The annular groove 124 is defined by a medial wall 126 that extends from the hemispherical surface 120 to an inner wall 130, and a lateral wall 128 that extends from the tapered surface 118 to the inner wall 130. As shown in FIGS. 6 and 7, the lateral wall 128 and the inner wall 130 define an angle 132, which is illustratively 70°. As described further below, in use, the annular groove 124 is configured to receive the annular flange 30 of the acetabular bearing 10 when the acetabular bearing 10 is fully installed in the acetabular shell component 100.

Figure 4:
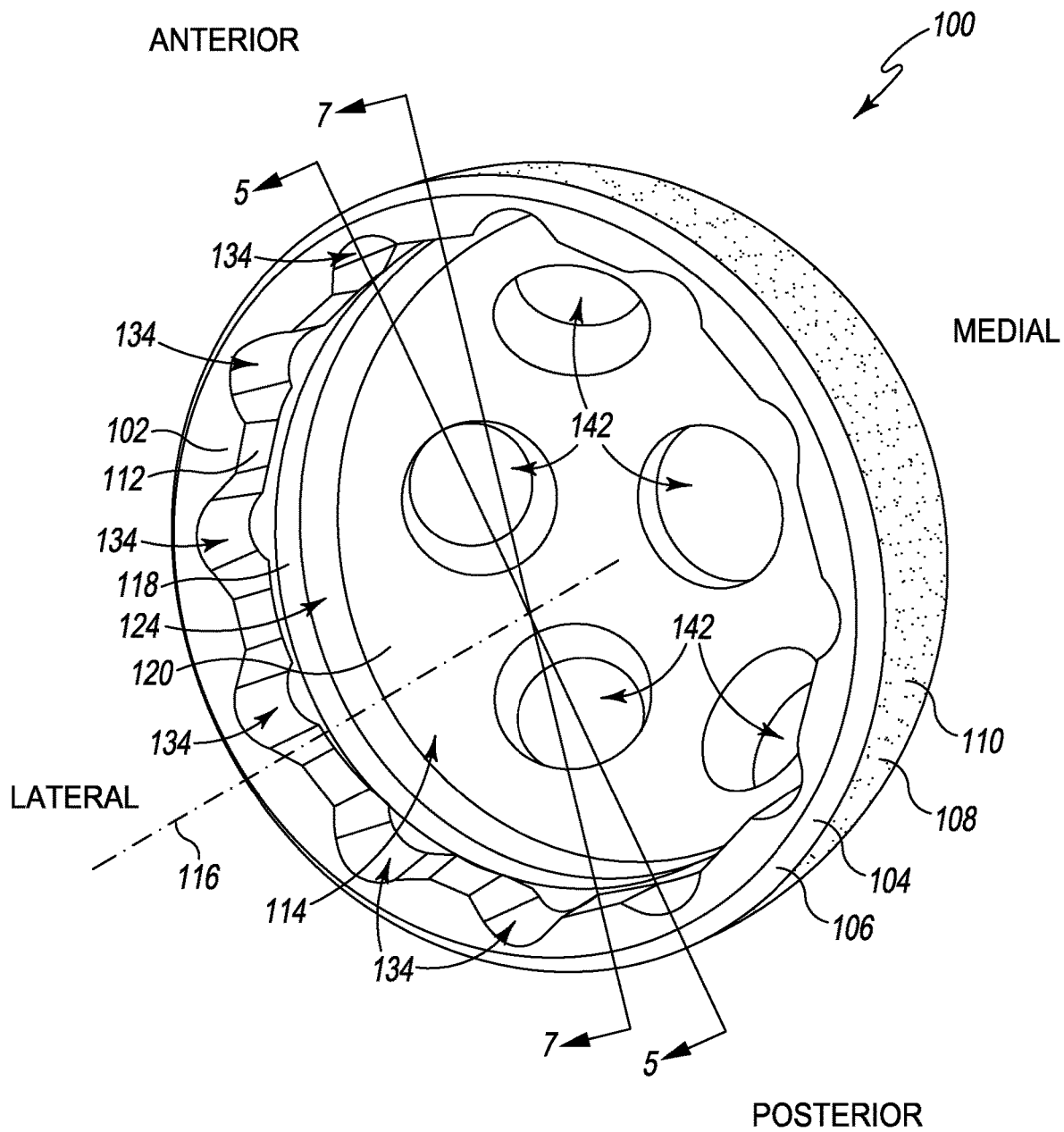
FIG. 4 is a perspective view of an acetabular shell component of an acetabular prosthetic implant.

As shown in FIGS. 4-6, a plurality of anti-rotation slots 134 are defined in the tapered surface 118 of the inner wall 112. The anti-rotation slots 134 are evenly distributed around the circumference of the tapered surface 118, and are shaped to receive corresponding anti-rotation keys 32 of the acetabular bearing 10. As shown, each anti-rotation slot 134 is defined by a medial wall 136 that extends from the tapered surface 118 to an inner wall 138. As shown in FIG. 6, the inner wall 138 blends smoothly into the tapered surface 118, and the medial wall 136 defines a ledge between the anti-rotation slot 134 and the tapered surface 118. As shown particularly in FIG. 7, an annular microgroove cutout 140 is further defined in the tapered surface 118. Each of the anti-rotation slots 134 extends into the annular microgroove cutout 140. As shown in FIGS. 4-5, in the illustrative embodiment, multiple slots 142 are defined through the surfaces 108, 120. In use, screws, pins, or other fasteners may be inserted through the slots 142 to secure the shell component 100 to the patient's bone.

Figure 8:
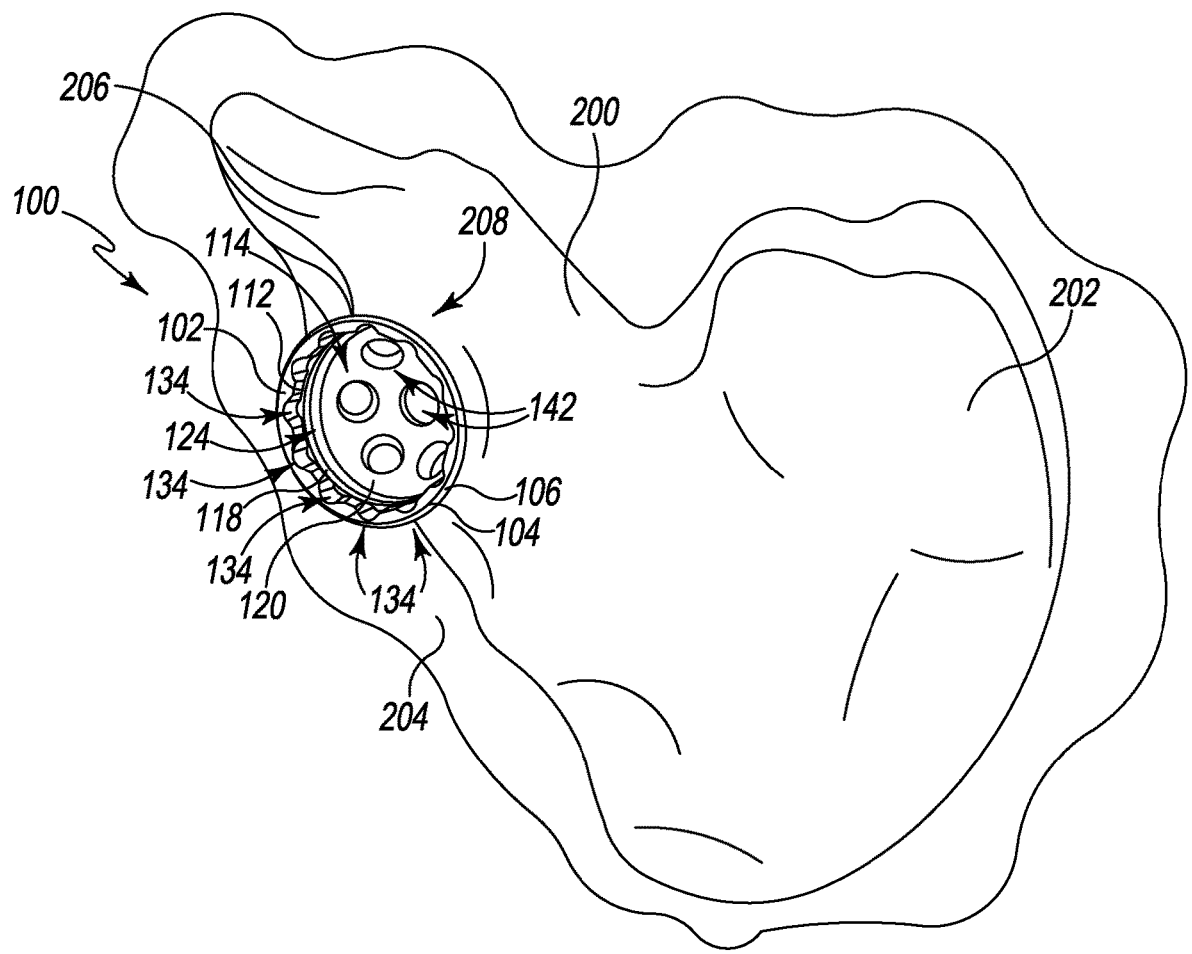
FIG. 8 is a perspective view showing the acetabular shell component of FIGS. 4-7 installed in a patient's hip.

Referring now to FIGS. 8-14, in use, the acetabular prosthesis of FIGS. 1-7 may be used during an orthopaedic surgical procedure. FIG. 8 illustrates a patient's hip bone 200. As shown, the hip bone 200 includes three parts, an ilium 202, an ischium 204, and a pubis 206, that define a natural acetabulum 208. To perform the orthopaedic surgical procedure, first, the surgeon surgically prepares the patient's bone to receive the acetabular shell component 100. For example, the surgeon may utilize a surgical reamer to prepare the patient's acetabulum 208 to receive the acetabular shell component 100. In some embodiments, the surgeon may also remove any existing acetabular component or other prosthetic components from the patient's bone. The surgeon next inserts the acetabular shell component 100 into the patient's surgically prepared acetabulum 208 and then impacts or otherwise installs the shell component 100 in the patient's bone 200. In some embodiments, one or more bone screws or other fasteners may be inserted through the slots 142 in order to attach the shell component 100 to the bone 200.

Figure 9:
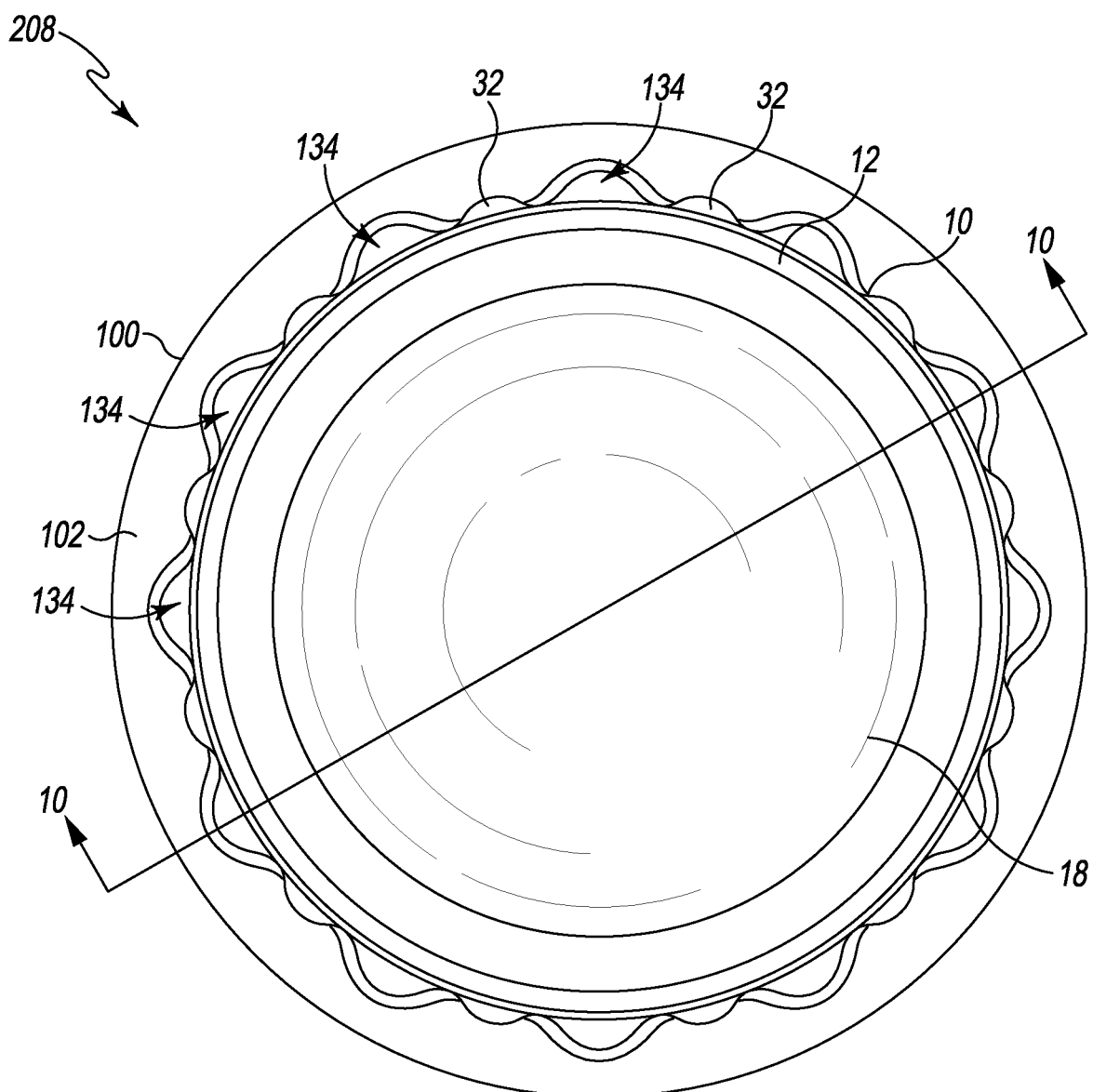
FIG. 9 is a plan view of the acetabular bearing component of FIGS. 1-3 positioned on the acetabular shell component installed in the patient's hip of FIG. 8.
Figure 10:
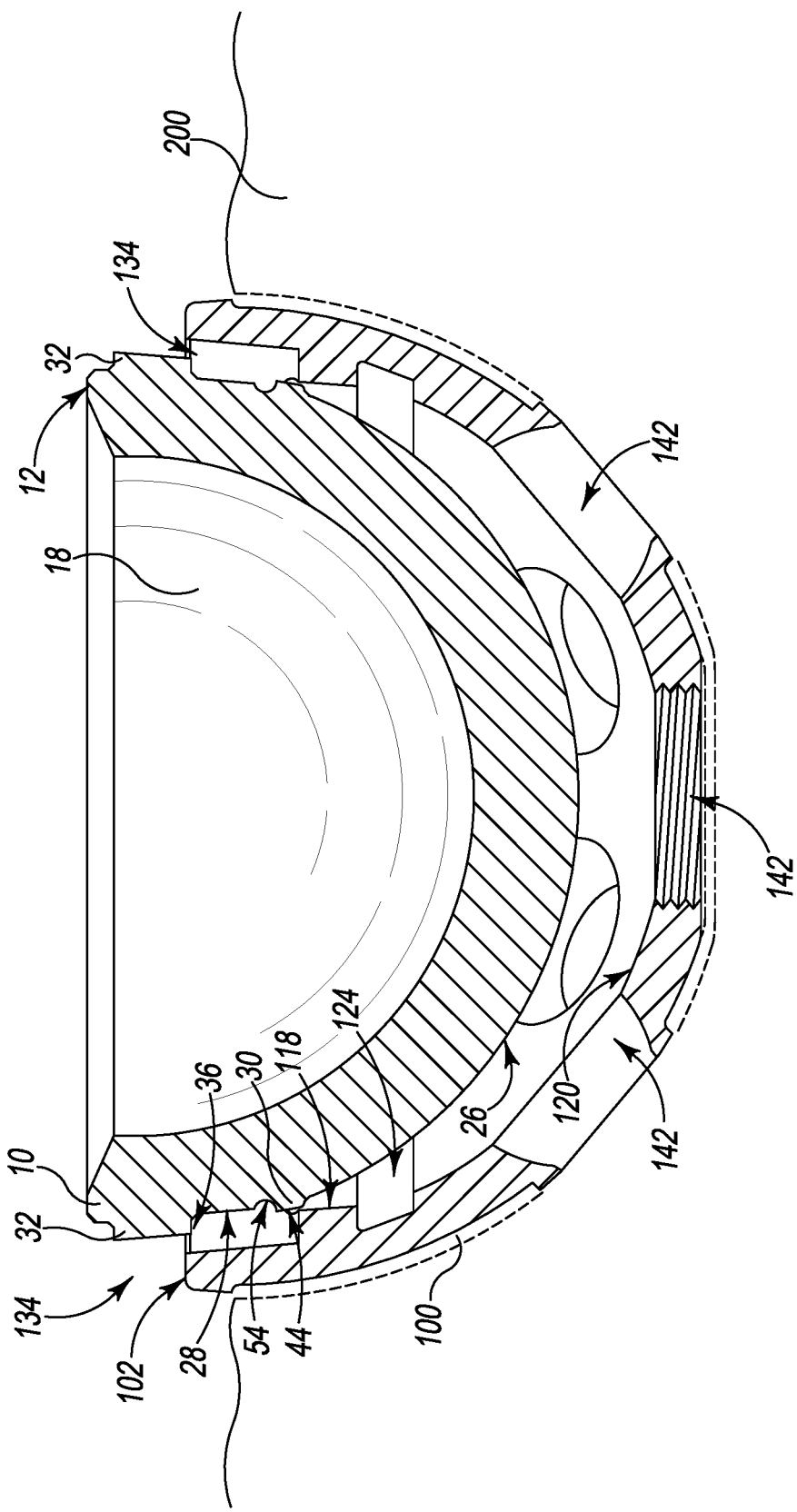
FIG. 10 is a cross-sectional view taken in the anterior-posterior direction along the line 10-10 of FIG. 9, as viewed in the direction of the arrows.

After fixing the acetabular shell component 100 to the bone 200, next, as shown in FIGS. 9-10, the surgeon places the acetabular bearing 10 on the acetabular shell component 100. As shown in FIG. 9, when the surgeon places the acetabular bearing 10 on the acetabular shell component 100, the anti-rotation keys 32 may not be in rotational alignment with the anti-rotation slots 134. As shown in FIG. 10, when the anti-rotation keys 32 are not in rotational alignment with the anti-rotation slots 134, the medial wall 36 of each anti-rotation key 32 contacts the annular rim 102 of the shell component 100 and causes the acetabular bearing 10 to remain partially inserted in the shell component 100. When the anti-rotation keys 32 are not be in rotational alignment with the anti-rotation slots 134, the flange surface 44 of the annular flange 30 is spaced apart from the tapered surface 118 of the shell component 100.

Figure 11:
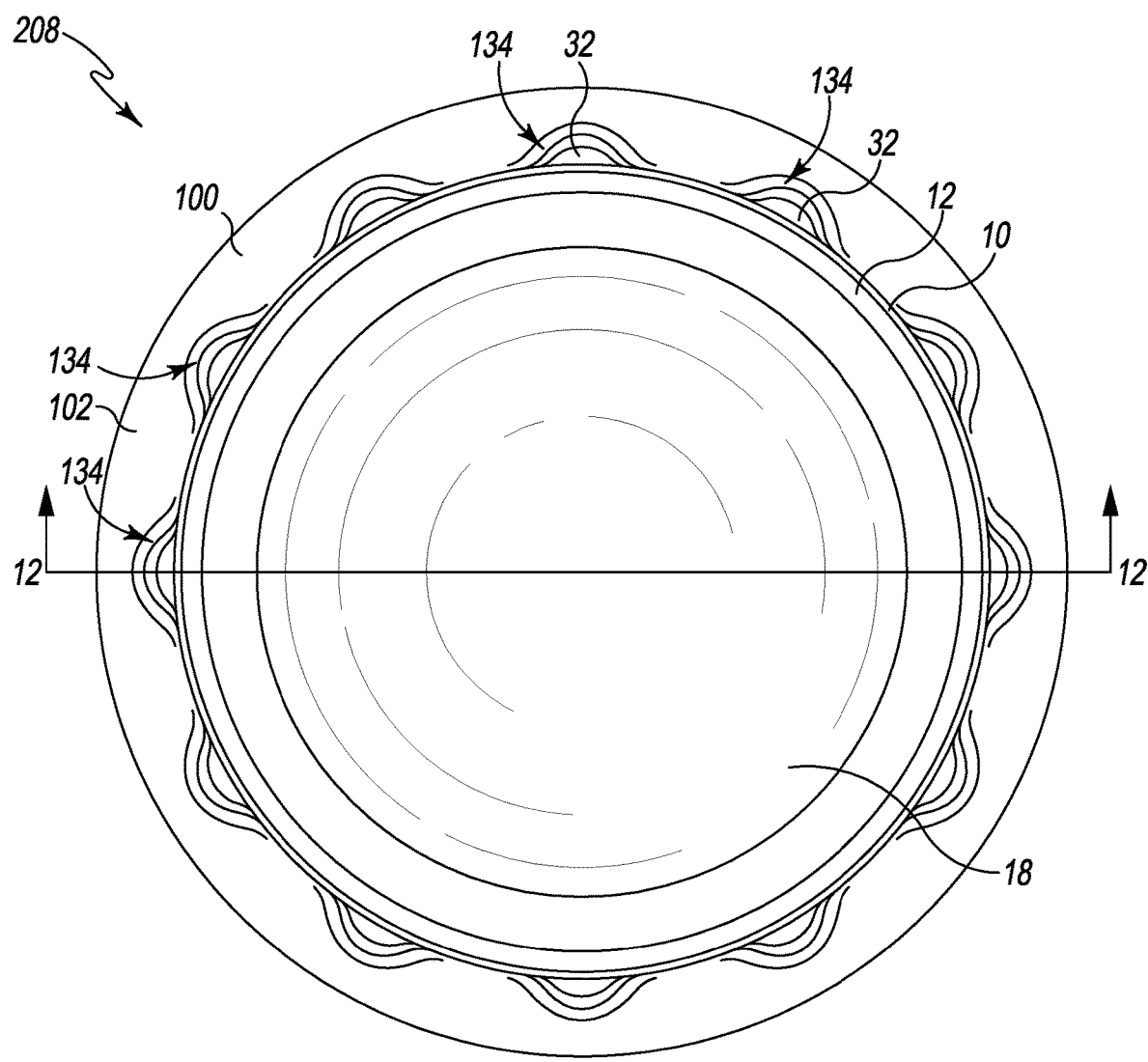
FIG. 11 is a plan view of the acetabular bearing component of FIGS. 1-3 positioned on and rotationally aligned with the acetabular shell component installed in the patient's hip of FIG. 10.
Figure 12:
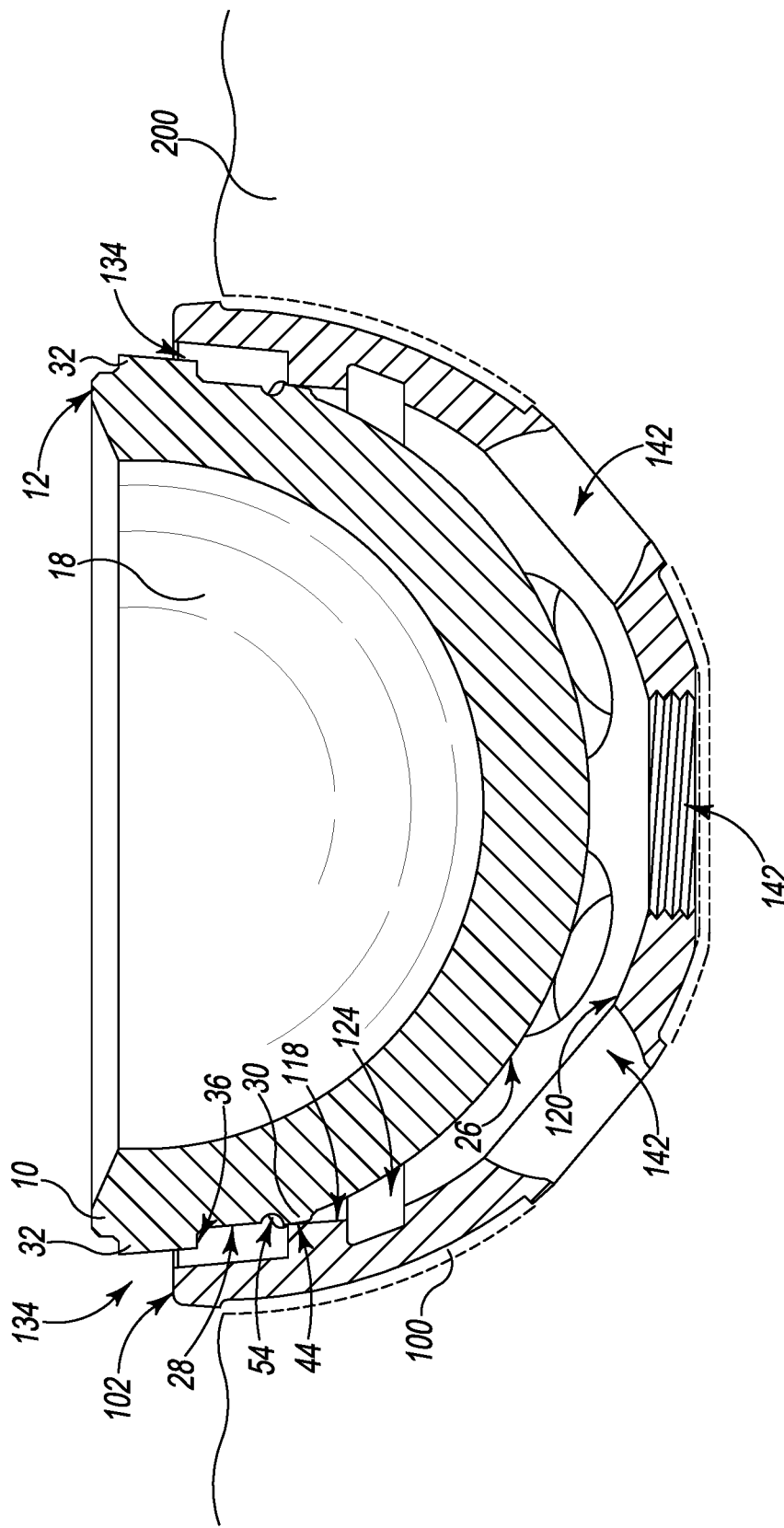
FIG. 12 is a cross-sectional view taken in the anterior-posterior direction along the line 12-12 of FIG. 11, as viewed in the direction of the arrows.

As shown in FIGS. 11-12, after placing the acetabular bearing 10 on the shell component 100, the surgeon rotates the bearing 10 until the anti-rotation keys 32 are aligned with the anti-rotation slots 134. When the anti-rotation keys 32 and the anti-rotation slots 134 are aligned, the acetabular bearing 10 drops further into the acetabular shell component 100 until the flange surface 44 of the annular flange is in contact with the tapered surface 118 of the shell component 100, as shown in FIG. 12. Additionally, and as shown, when the anti-rotation keys 32 and the anti-rotation slots 134 are aligned, each anti-rotation key 32 also partially enters a corresponding anti-rotation slot 134. That is, when aligned, the medial wall 36 of each anti-rotation key 32 is positioned below the annular rim 102 and within the corresponding anti-rotation slot 134. Accordingly, by dropping further into the shell component 100 and contacting the tapered surface 118, the acetabular bearing 10 provides feedback to the surgeon when the 10 the anti-rotation keys 32 are rotationally aligned with the anti-rotation slots 134.

Figure 13:
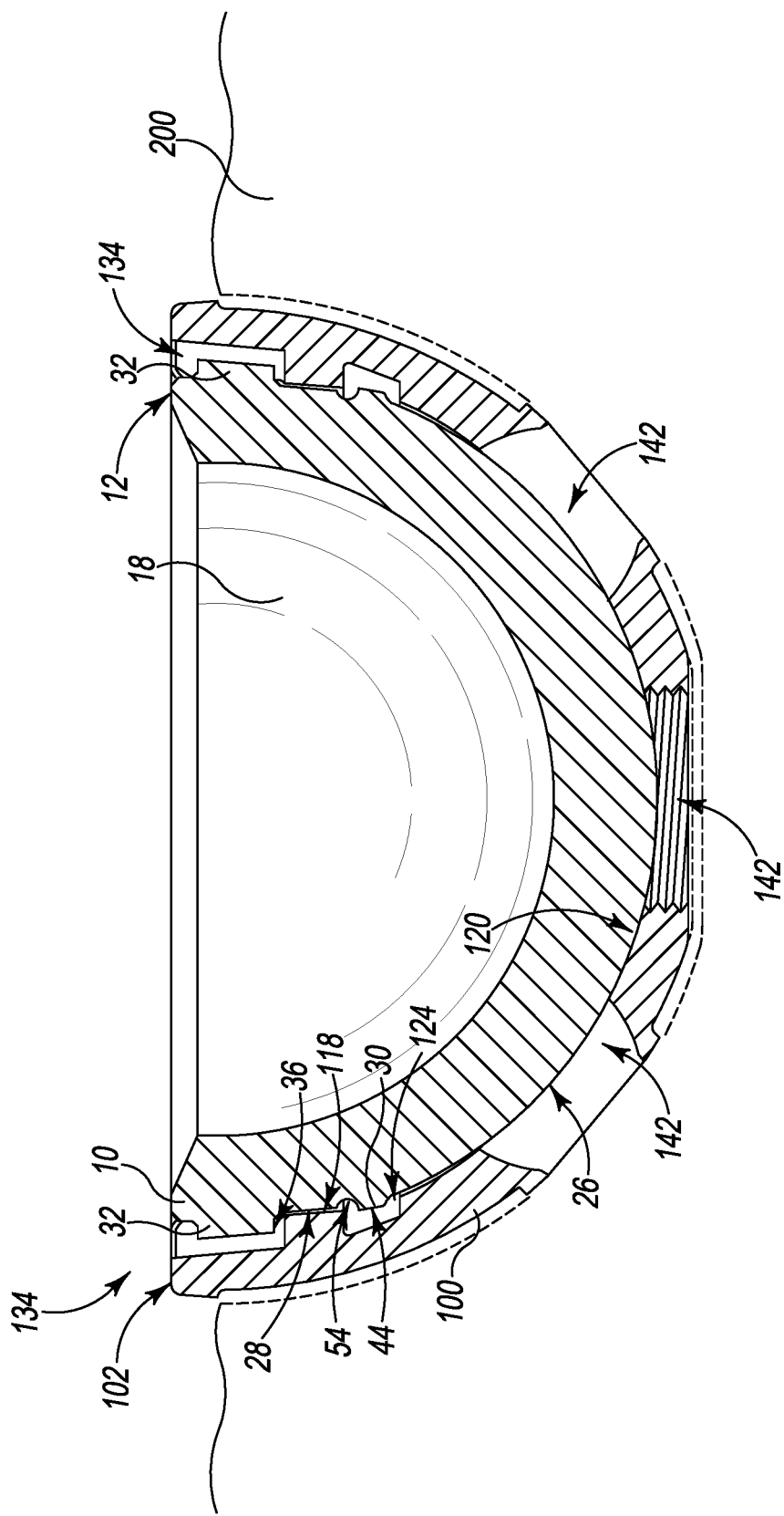
FIG. 13 is a cross-sectional view taken in the anterior-posterior direction of the acetabular bearing component of FIGS. 4-7 fully installed in the acetabular shell component installed in the patient's hip of FIG. 8.
Figure 14:
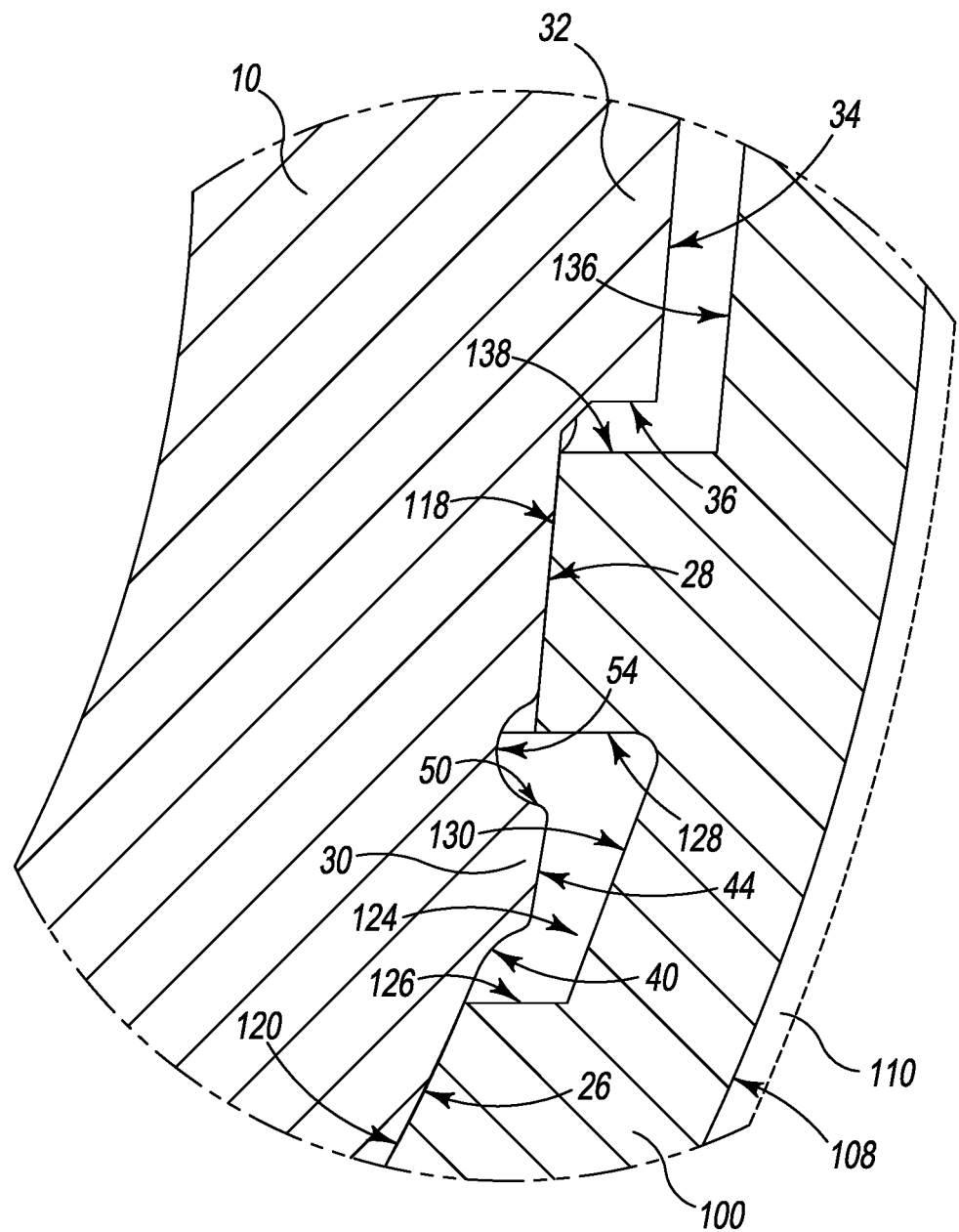
FIG. 14 is a detail view of the cross-sectional view of FIG. 13.

Once the anti-rotation keys 32 and the anti-rotation slots 134 are aligned, the surgeon impacts or otherwise advances the acetabular bearing 10 into the shell component 100. As the acetabular bearing 10 is inserted into the shell component 100, the flange 30 is deformed by force exerted by the tapered surface 118 on the flange surface 44. The surgeon continues advancing the acetabular bearing 10 into the shell component 100 until the acetabular bearing is fully inserted, as shown in FIGS. 13-14. When the acetabular bearing 10 is fully installed, the flange 30 returns to its original shape. The flange 30 does not experience plastic deformation, damage, or other changes in shape after being fully installed.

As shown in the detailed view of FIG. 14, when the acetabular bearing 10 is fully installed in the shell component 100, the tapered surface 28 of the bearing 10 is in contact with the tapered surface 118 of the shell component 100, and the hemispherical surface 26 of the acetabular bearing 10 is in contact with the hemispherical surface 120 of the shell component 100. The bearing 10 is retained in the shell component 100 by a friction lock between the tapered surfaces 28, 118.

Additionally, when the acetabular bearing 10 is fully installed, the annular flange 30 of the bearing 10 is received by the annular groove 124 of the shell component 100. When fully installed, the surfaces 40, 44, 50 of the annular flange 30 may not be in contact with the walls 126, 128, 130 that define the annular groove 124. The annular flange 30 and the annular groove 124 cooperate to retain the acetabular bearing 10 within the shell component 100 and thereby improve pull-out resistance and spin-out resistance of the bearing 10. For example, if the bearing 10 starts to slide laterally out of the acetabular bearing 100, then the back edge surface 50 of the acetabular bearing 10 contacts the lateral wall 128 of the acetabular shell component 100, thereby retaining the annular flange 30 and increasing pull-out resistance of the bearing 10. Similarly, if the bearing 10 starts to rotate such that the bearing 10 slides medially relative to the shell component 100 as viewed in FIG. 14, then the lead-in surface 40 and/or the flange surface 44 of the acetabular bearing 10 contacts the medial wall 126 of the acetabular shell component 100, thereby retaining the annular flange 30 and increasing spin-out resistance of the bearing 10.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the devices and assemblies described herein. It will be noted that alternative embodiments of the devices and assemblies of the present disclosure may not include all of the features described yet still benefit from at least some of the advantages of such features. Those of ordinary skill in the art may readily devise their own implementations of the devices and assemblies that incorporate one or more of the features of the present invention and fall within the spirit and scope of the present disclosure as defined by the appended claims.

The invention claimed is:

1. An acetabular prosthesis assembly comprising:
an acetabular shell component configured to be implanted in a surgically-prepared acetabulum of a patient, the acetabular shell component comprising an annular rim and a concave inner wall extending medially from the annular rim, the concave inner wall having a tapered surface with a plurality of anti-rotation slots defined therein; and
a polymeric acetabular bearing component configured to be received by the acetabular shell component, the acetabular bearing component comprising (i) an annular rim, (ii) a convex outer wall extending medially from the annular rim to an apex, (iii) an annular flange extending radially outward from the outer wall, and (iv) a plurality of anti-rotation keys extending radially outward from the outer wall, wherein the plurality of anti-rotation keys are spaced evenly around the annular rim of the acetabular bearing component;
wherein: (i) when the plurality of anti-rotation keys are positioned in rotational alignment with the plurality of anti-rotation slots, the flange of the acetabular bearing component is positioned in contact with the tapered surface of the acetabular shell component, and (ii) when the plurality of anti-rotation keys are positioned out of rotational alignment with the plurality of anti-rotation slots, the flange of the acetabular bearing component is spaced apart from the tapered surface of the acetabular shell component; and
wherein the outer wall of the acetabular bearing component comprises a tapered surface extending medially from the annular rim to a curved relief surface positioned between the tapered surface and the flange, wherein the tapered surface, when viewed in a cross-sectional plane taken in an anterior-posterior direction, defines a first imaginary line that extends along the tapered surface and the curved relief surface extends radially inward relative to the first imaginary line from the tapered surface and the flange.

2. The acetabular prosthesis assembly of claim 1, wherein when the plurality of anti-rotation keys are positioned out of rotational alignment with the plurality of anti-rotation slots, a medial surface of each of the plurality of anti-rotation keys is positioned in contact with the annular rim of the acetabular shell component.

3. The acetabular prosthesis assembly of claim 2, wherein when the plurality of anti-rotation keys are positioned in rotational alignment with the plurality of anti-rotation slots, the medial surface of each of the plurality of anti-rotation keys is positioned within a corresponding anti-rotation slot of the plurality of anti-rotation slots.

4. The acetabular prosthesis assembly of claim 3, wherein when the plurality of anti-rotation keys are positioned in rotational alignment with the plurality of anti-rotation slots, the medial surface of each of the plurality of anti-rotation keys is positioned medially by a predetermined distance from the annular rim of the acetabular shell component.

5. The acetabular prosthesis assembly of claim 4, wherein the predetermined distance comprises 0.5 millimeters.

6. The acetabular prosthesis assembly of claim 1, wherein when the plurality of anti-rotation keys are positioned in rotational alignment with the plurality of anti-rotation slots and the acetabular bearing component is fully installed in the acetabular shell component, each of the plurality of anti-rotation keys is positioned within a corresponding anti-rotation slot of the plurality of anti-rotation slots.

7. The acetabular prosthesis assembly of claim 6, wherein when the plurality of anti-rotation keys are positioned in rotational alignment with the plurality of anti-rotation slots and the acetabular bearing component is fully installed in the acetabular shell component, the flange is received in an annular groove defined in the concave inner wall of the acetabular shell component.

8. The acetabular prosthesis assembly of claim 1, wherein the plurality of anti-rotation keys extend radially outward from the tapered surface.

9. The acetabular prosthesis assembly of claim 1, wherein:
the tapered surface of the acetabular shell component defines a taper angle; and
the flange of the acetabular bearing component comprises a flange surface that defines a flange angle, wherein the flange angle is greater than or equal to the taper angle.

10. The acetabular prosthesis assembly of claim 9, wherein the taper angle is 10° and the flange angle is between 10-14°.

11. The acetabular prosthesis assembly of claim 10, wherein the flange angle is 12°.

12. A method for installing an acetabular prosthesis, the method comprising:
implanting an acetabular shell component into a surgically-prepared acetabulum of a patient, wherein the acetabular shell component comprises an annular rim and a concave inner wall extending medially from the annular rim, the concave inner wall having a tapered surface with a plurality of anti-rotation slots defined therein;
moving an acetabular bearing component into contact with the implanted acetabular shell component, wherein the acetabular bearing component comprises (i) an annular rim, (ii) a convex outer wall extending medially from the annular rim to an apex, (iii) an annular flange extending radially outward from the outer wall, and (iv) a plurality of anti-rotation keys extending radially outward from the outer wall, wherein the plurality of anti-rotation keys are spaced evenly around the annular rim of the acetabular bearing component; and rotating the acetabular bearing component relative to the implanted acetabular shell component from a first position in which the plurality of anti-rotation keys are positioned out of rotational alignment with the plurality of anti-rotation slots to a second position in which the plurality of anti-rotation keys are positioned in rotational alignment with the plurality of anti-rotation slots, wherein when in the first position the flange of the acetabular bearing component is spaced apart from the tapered surface of the acetabular shell component, and when in the second position the flange of the acetabular bearing component is positioned in contact with the tapered surface of the acetabular shell component;

wherein the outer wall of the acetabular bearing component comprises a tapered surface extending medially from the annular rim to a curved relief surface positioned between the tapered surface and the flange, wherein the tapered surface, when viewed in a cross-sectional plane taken in an anterior-posterior direction, defines a first imaginary line that extends along the tapered surface and the curved relief surface extends radially inward relative to the first imaginary line from the tapered surface and the flange.

13. The method of claim 12, further comprising impacting the acetabular bearing component into the implanted acetabular shell component once the acetabular bearing component is in the second position.

14. The method of claim 13, wherein impacting the acetabular bearing component comprises deforming the flange of the acetabular bearing component.

15. The method of claim 14, further comprising receiving the flange of the acetabular bearing component in an annular groove defined in the concave inner wall of the acetabular shell component.

16. The method of claim 15, wherein receiving the flange in the annular groove comprises elastomerically relaxing the flange to its original shape.

17. The method of claim 15, wherein receiving the flange in the annular groove comprises engaging a tapered surface of the acetabular bearing component with the tapered surface of the acetabular shell component.

* * * * *